United States Patent [19]

Koeda et al.

[11] 4,083,850
[45] Apr. 11, 1978

[54] 3-SUBSTITUTED-2(1H)PYRIDON-6-CARBOXYLIC ACIDS AND PROCESS FOR PREPARATION OF SAME

[75] Inventors: Takemi Koeda, Yokohama; Takashi Tsuruoka, Kawasaki; Hiroyasu Asaoka, Yokohama; Uichi Shibata, Tokyo; Shigeharu Inoue; Taro Niida, both of Yokohama, all of Japan

[73] Assignee: Meiji Seika Kaisha Ltd., Japan

[21] Appl. No.: 700,340

[22] Filed: Jun. 28, 1976

[30] Foreign Application Priority Data

Jun. 30, 1975 Japan .................................. 50-80102
Jun. 30, 1975 Japan .................................. 50-80103

[51] Int. Cl.² ............................................ C07D 213/55
[52] U.S. Cl. ........................... 260/295.5 R; 260/295 R
[58] Field of Search ...................... 260/295.5 R, 295 R

[56] References Cited

U.S. PATENT DOCUMENTS 3,956,337   5/1976   Niwa et al. ...................... 260/293.86

OTHER PUBLICATIONS

Shukla et al., Chem. Abstracts, vol. 81 (1), item no. 1160m, July 8, 1974.

*Primary Examiner*—Alan L. Rotman
*Attorney, Agent, or Firm*—McGlew and Tuttle

[57] ABSTRACT

Novel compounds useful as hypotensive agents are presented having the general formula I

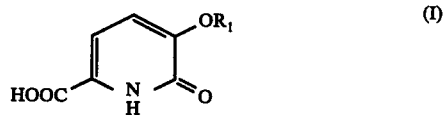

wherein $R_1$ represents a lower aliphatic acyl group, a straight or branched chain alkyl or alkenyl group or an aralkyl group of the general formula

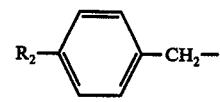

wherein $R_2$ represents hydrogen, a lower alkyl group or a halogen atom. Furthermore, new therapeutic compositions of matter are also described incorporating the above novel 3-substituted-2(1H)pyridone-6-carboxylic acids (I) as an active ingredient with carriers and showing uses as hypotensive agents. These new compounds of the formula I are prepared either by reacting D-glucaro-δ-lactam or its salt with an acid anhydride or by reacting 3-hydroxy-2(1H)pyridone-6-carboxylic acid with an acyl anhydride or alkyl halide, aralkyl halide and an alkenyl halide.

27 Claims, No Drawings

3-SUBSTITUTED-2(1H)PYRIDON-6-CARBOXYLIC ACIDS AND PROCESS FOR PREPARATION OF SAME

DESCRIPTION OF THE INVENTION

This invention relates to 3-substituted-2(1H)pyridone-6-carboxylic acids, a process for the preparation of same, and therapeutic compositions of matter formed from the same.

An object of the present invention is to provide 3-substituted-2(1H)pyridone-6-carboxylic acids of the general formula I

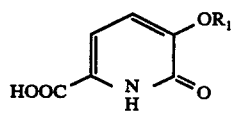 (I)

wherein $R_1$ stands for a lower aliphatic acyl group, a straight or branched alkyl or alkenyl group or an aralkyl group of the formula

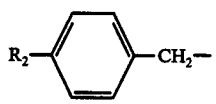

wherein $R_2$ stands for hydrogen, a lower alkyl group or a halogen atom. Generally, the preferred $R_1$ groups contain the lower alkyl (straight or branched) as well as the lower alkenyl, ar-(lower) alkyl, and the lower aliphatic acyl, where "lower" means a group having from one to six carbon atoms.

A further object of the present invention is to provide advantageous processes for the preparation of the compounds I.

Another object is to provide compositions useful in lowering blood pressure in mammals.

Thus, according to the present invention, the compounds of the formula I wherein $R_1$ stands for a lower aliphatic acyl group can be prepared by reacting D-glucaro-δ-lactam or its salt with a lower aliphatic carboxylic acid anhydride. This method will be hereinafter referred to as Method 1. The compounds of the formula I wherein $R_1$ stands for a straight or branched alkyl or alkenyl group or an aralkyl group of the formula

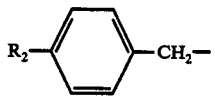

wherein $R_2$ has the same meaning as described above can be prepared by reacting 3-hydroxy-2(1H) pyridone-6-carboxylic acid of the formula II

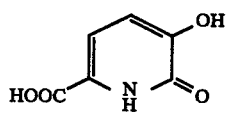 (II)

with an alkyl, alkenyl, or aralkyl halide of the general formula III $R_1X$ (III)

wherein $R_1$ stands for the same meaning as described just above and X stands for a halogen atom. This method will be hereinafter referred to as Method 2.

D-glucaro-δ-lactam, one of the starting materials for Method 1, is easily available, for example by oxidation of antibiotic Nojirimycin in accordance with the method which was also found by us. (See U.S. Pat. No. 3,956,337, col. 3, lines 40–45).

When D-glucaro-δ-lactam in the form of free acid or its salt such as sodium or potassium salt is treated in pyridine with an acid anhydride in the cold or at room temperature (e.g. at temperatures of 0°–25° C), the corresponding tetraacyl derivative results as expected.

It has now been surprisingly found that when this reaction is carried out under heating a dehydration reaction takes place to form the corresponding 3-acyloxy-2(1H)pyridone-6-carboxylic acid.

In carrying out Method 1, D-glucaro-δ-lactam, which may be used in the form of free acid or its salt such as sodium or potassium salt, is treated with an acid anhydride in the presence of a base to cause acylation and dehydration reactions to take place simultaneously. Suitable examples of the base for this purpose include pyridine, triethylamine and piperidine. The reaction may be carried out in the presence of a solvent such as dimethylformamide or dioxan, i.e. by dissolving or suspending therein the reactants. The most satisfactory yield is obtainable when D-glucaro-δ-lactam or its salt is treated with an acid anhydride in the presence of pyridine as both solvent and base. The reaction temperature is required to be higher than those for ordinary acylation reactions. A suitable temperature range is from 40° to 100° C. The reaction time depends upon the reaction temperature. In general, when D-glucaro-δ-lactam is used on the form of free acid, the reaction will be complete in 5–7 hours at a reaction temperature of 55° C. When D-glucaro-δ-lactam is used in the form of its metal salt such as its potassium or sodium salt, a longer reaction time, for example 70–80 hours at a reaction temperature of 80° C, is required due to less solubility of the salt, although higher yields are in general obtained.

3-Hydroxy-2(1H) pyridone-6-carboxylic acid, one of the starting materials for Method 2, is easily available for example by deacylation of a 3-acyloxy-2(2H)pyridone-6-carboxylic acid which can be prepared as described above.

In carrying out Method 2, 3-hydroxy-2(1H)pyridone-6-carboxylic acid of the formula II is reacted in a solvent and a base with an alkyl, alkenyl or aralkyl halide of the general formula III to cause selective substitution at the 3-hydroxyl group. Suitable examples of the solvent include water, organic solvents miscible with water and mixtures of them such as water/an alcohol, water/dioxan, water/acetone or the like. Suitable examples of the base include inorganic bases such as sodium hydroxide, potassium hydroxide, sodium carbonate, potassium carbonate or sodium hydrogen carbonate, and organic bases such as triethylamine.

In this reaction little substitution at the >NH in the pyridone ring is found to take place, which is considered to be due to steric hindrance by the 6-carboxyl group.

This reaction proceeds also in an organic solvent such as alcohols, dioxan or acetone, although in this case a substitution reaction at the carboxyl group takes place simultaneously. It is of course possible to convert the thus formed esters into the desired compounds in an easy manner, for example by hydrolysis with an acid or alkali.

When an alkyl halide is used, the reaction temperature is preferably in the range of from 40° to 100° C. When an alkenyl or aralkyl halide is used, the reaction proceeds smoothly at a temperature of from room temperature to 70° C.

Some of the halides may cause more or less side-reaction products to form, which, however, can be removed easily by any suitable work-up operation, such as solvent extraction, precipitation or crystallization.

The compounds according to the present invention all show a hypotensive effect and therefore are useful as pharmaceuticals.

With a view to exhibiting the hypotensive effect of the compounds of the invention, the following pharmacological test was conducted for some examples of the compounds:

To a group consisting of three to five 20–25 week old rats having spontaneous hypertension was administered, either intraperitoneally or orally, each of the compounds to be tested suspended in a 1% gum arabic (acacia) solution. The change of blood pressure was measured in each case by the tail volume method to give the following results:

tered off to obtain 8.9 g of potassium 3-acetoxy-2(1H)pyridone-6-carboxylate as white needle crystals.

Melting point: 234°–235° C (dec.)

Elemental analysis: Found (%): C 41.02, H 2.49, N 5.73; Calcd. for $C_8H_6O_5NK$(%): C 40.84, H 2.57, N 5.95

5 g of the potassium salt was dissolved in 120 cc of distilled water. The solution was adjusted to pH 2 with 1N hydrochloric acid and concentrated at a temperature below 40° C to approximately 20 cc to precipitate crystals. The crystals were filtered off and dried in a desiccator to obtain 3.6 g of the corresponding free acid, 3-acetoxy-2(1H)-pyridone-6-carboxylic acid, as white needle-like crystals.

Melting point: 211°–213° C

Elemental Analysis: Found (%): C 48.15, H 3.43, N 7.19; Calcd. for $C_8H_7O_5N$(%): C 48.74, H 3.58, N 7.11

EXAMPLE 2

5 g of D-glucaro-δ-lactam as free acid was dissolved in a mixture of 50 cc. of pyridine and 22 cc. of acetic anhydride and heated to 60° for 70 hours. The reaction mixture was immediately concentrated to dryness and the residue washed with ether, dissolved in 100 cc. of distilled water and decolored with active carbon. The decolored solution was adjusted to pH 2 with 1N hy-

| Compound | Dose in mg/kg | Route of adminstration | Blood pressure before administration in mmHg | Blood pressure after administration in mmHg | | | |
|---|---|---|---|---|---|---|---|
| | | | | After 1 hr. | After 2 hrs. | After 4 hrs. | After 6 hrs. |
| 3-Acetoxy-2(1H)pyridone-6-carboxylic acid | 300 | oral | 197 | — | — | 181 | 160 |
| 3-Propionyloxy-2(1H)-pyridone-6-carboxylic acid | 50 | intraperitoneal | 190 | 173 | 172 | 179 | — |
| 3-Butyryloxy-2(1H)-pyridone-6-carboxylic acid | 100 | " | 188 | 174 | 173 | 176 | — |
| 3-n-propyloxy-2(1H)-pyridone-6-carboxylic acid | 200 | " | 175 | 148 | 146 | 150 | 155 |
| 3-n-Butyloxy-2(1H)-pyridone-6-carboxylic acid | 50 | " | 195 | 173 | 177 | 182 | — |
| 3-Allyloxy-2(1H)pyridone-6-carboxylic acid | 200 | " | 197 | 154 | 158 | 156 | 178 |
| 3-(p-Ethylbenzyloxy)-2(1H)pyridone-6-carboxylic acid | 50 | " | 185 | — | 172 | 161 | 168 |

EXAMPLE 1

60 g of the potassium salt of D-glucaro-δ-lactam was suspended in 500 cc. of pyridine and 250 cc. of acetic anhydride and the suspension stirred at 80° C. The starting material, the potassium salt of D-glucaro-δ-lactam, was slowly dissolved and subsequently the dehydrated product, potassium 3-acetoxy-2(1H) pyridone-6-carboxylate, precipitated. The reaction was complete in approximately 70 hours, which was confirmed by tracing by means of thin layer chromatography on silica gel. The reaction mixture was cooled to 5°–10° C and filtered and the resulting solid product was washed with cold acetone and dried in a desiccator to obtain 60 g of potassium 3-acetoxy-2(1H)pyridone-6-carboxylate as crude crystals.

10 g of the crude crystals were dissolved in 300 cc of distilled water and decolored with active carbon. The subsequent concentration to approximately 50 cc caused precipitation of crystals. The crystals were fildrochloric acid and concentrated to approximately 15 cc. to precipitate crystals. The crystals were filtered off to obtain 1.3 g of 3-acetoxy-2(1H)pyridone-6-carboxylic acid as free acid.

EXAMPLE 3

5 g of the potassium salt of D-glucaro-δ-lactam was suspended in a mixture of 60 cc. of pyridine and 25 cc. of propionic anhydride and the reaction was carried out with stirring at 75° C for 80 hours. The precipitated potassium 3-propionyloxy-2(1H) pyridone-6-carboxylate was cooled, filtered off and washed with cold ethanol.

The product was dissolved in 150 cc. of distilled water and the solution decolored with active carbon, adjusted to pH 2 with 1N hydrochloric acid and concentrated to approximately 20 cc to precipitate crystals. The crystals were filtered off to obtain 3.5 g of 3-propionyloxy-2(1H)pyridone-6-carboxylic acid as white powder.

Melting point: 182°–183° C.
Elemental analysis: Found (%): C 51.82, H 4.37, N 6.59; Calcd. for $C_9H_9O_5N$ (%): C 51.19, H 4.30, N 6.63

EXAMPLE 4

2 g of the sodium salt of D-glucaro-δ-lactam was suspended in a mixture of 30 cc. of pyridine and 20 cc. of butyric anhydride and the reaction carried out with stirring at 90° C for 50 hours.

After cooling the reaction mixture, the formed precipitate of sodium 3-butyryloxy-2(1H)pyridone-6-carboxylate was filtered off and washed with cooled ethanol. Yield 2.2 g.

The product was dissolved in a mixture of 100 cc of distilled water and 40 cc. of methanol and the solution decolored with active carbon and concentrated to approximately 25 cc to precipitate crystals. The crystals were filtered off to obtain 1.8 g of sodium 3-butyryloxy-2(1H)pyridone-6-carboxylate as white powder.

Melting point: 193°–196° C (dec.)
Elemental analysis: Found (%): C 48.37, H 3.98, N. 5,48; Calcd. for $C_{10}H_{10}O_5NNa$(%): C 48.59, H 4.08, N 5.67

EXAMPLE 5

52 g of 3-acetoxy-2(1H)pyridone-6-carboxylic acid was suspended in 500 cc of distilled water and 20 g of sodium hydroxide added to the suspension. The mixture was warmed to 60° C for 30 minutes. The resulting reaction mixture was adjusted to pH 2 with 5N hydrochloric acid, whereupon crystals are immediately precipitated. After the reaction mixture was allowed to stand in the cold, the crystals were filtered off and dried in a desiccator to obtain 45 g of 3-hydroxy-2(1H)pyridone-6-carboxylic acid in the form of white needle crystals.

A sample recrystallized from hot water was analyzed to give the following results:

Melting point: 248°–249° C
Elemental Analysis: Found (%): C 41.48, H 3.89, N 8.15; Calcd. for $C_6H_5O_4N \cdot H_2O$(%): C 41.62, H 4.08, N 8.09

EXAMPLE 6

9.3 g of 3-hydroxy-2(1H)pyridone-6-carboxylic acid was suspended in 200 cc. of distilled water. When 5 g of sodium hydroxide was added to the suspension, the carboxylic acid dissolved. To the mixture was added dropwise, with stirring at 65° C over a period of 5 hours, n-propyl bromide dissolved in 59 cc. of ethanol. After being kept at the same temperature for an additional thirty hours, the reaction mixture was concentrated to approximately 150 cc and adjusted to pH 2 with 5N hydrochloric acid to precipitate crystals. The crystals were recrystallized from chloroform/ethanol to obtain 9.8 g of 3-n-propyloxy-2(1H)pyridone-6-carboxylic acid in the form of white crystals.

Melting point: 247°–248° C
Elemental analysis: Found (%): C 53.98, H 5.17, N 6.96; Calcd. for $C_9H_{11}O_4N$(%): C 54.82, H 5.62, N 7.10

EXAMPLE 7

1.5 g of 3-hydroxy-2(1H)pyridone-6-carboxylic acid was added to a mixture of 30 cc of distilled water and 20 cc of methanol. After addition of 1.3 g of potassium hydroxide followed by that of 4 cc of n-butyl iodide, the reaction was carried out with stirring at 60° C for 20 hours.

The reaction mixture (pH 8) was concentrated to approximately 20 cc and extracted with 5 cc of chloroform to remove impurities. The aqueous phase was adjusted to pH 2 with 5N hydrochloric acid and extracted with 20 cc of chloroform. The extract was concentrated to approximately 3 cc. After addition of 5 cc of ethanol, the concentrate was allowed to stand in the cold, whereupon crystals formed. The crystals were filtered off to obtain 980 mg of 3-n-butyloxy-2(1H)-pyridone-6-carboxylic acid in the form of crystals.

Melting point: 198°–200° C
Elemental analysis: Found (%): C 55.71, H 6.45, N 6.24; Calcd. for $C_{10}H_{13}O_4N$(%): C 56.86, H 6.20, N 6.63

EXAMPLE 8

40 cc of distilled water was added to 1.6 g of 3-hydroxy-2(1H)-pyridone-6-carboxylic acid and 3 g of sodium carbonate. To this mixture was added dropwise, with stirring at 70° C over a period of 5 hours, 5 cc of isopropyl bromide dissolved in 10 cc of acetone. After being kept at the same temperature for an additional 30 hours with stirring, the reaction mixture was concentrated to approximately 15 cc and adjusted to pH 1.8 with 5N hydrochloric acid, whereupon precipitation took place. The precipitate was crystallized from methanol/ethanol to obtain 1.3 g of 3-isopropyloxy-2(1H) pyridone-6-carboxylic acid in the form of white crystals.

Melting point: 206°–209° C
Elemental analysis: Found (%): C 54.65, H 5.45, N 7.17; Calcd. for $C_9H_{11}O_4N$(%): C 54.82, H 5.62, N 7.10

EXAMPLE 9

4.5 g of 3-hydroxy-2(1H)pyridone-6-carboxylic acid was suspended in 100 cc of distilled water. After addition of 3.5 g of sodium carbonate and 6 g of allyl bromide, the mixture was stirred at 60° C for one hour. The reaction mixture was adjusted to pH 1.5 with 5N hydrochloric acid, whereupon a crystalline precipitate formed. The mixture was extracted directly with 50 cc of chloroform. The extract was concentrated to approximately 10 cc and the concentrate, after addition of 20 cc of ethanol, was allowed to stand in the cold to precipitate crystals. The crystals were filtered off to obtain 5.2 g of 3-allyloxy-2(1H)pyridone-6-carboxylic acid in the form of white crystals.

Melting point: 203°–204° C
Elemental analysis: Found (%): C 53.82, H. 4.52, N 7.41; Calcd. for $C_9H_9O_4N$ (%): C 55.38, H 4.65, N 7.18

In a like manner 3-(2-methyl-1-propenyloxy)-2(1H)pyridone-6-carboxylic acid may be prepared by mixing about 5 g of 3-hydroxy-2(1H)pyridone-6-carboxylic acid in 100 cc of distilled water. After addition of 3.5 g of sodium carbonate and about 7 g of 2-methyl-1-propenyl bromide, the mixture is stirred with heating. The reaction mixture is made acid by addition of 5N hydrochloric acid as above. The resulting mixture is extracted with chloroform. As above this extract is concentrated and ethanol is added. The resulting mixture is allowed to stand in the cold to precipitate crystals which are separated from the mixture by filtration.

EXAMPLE 10

1.5 g of 3-hydroxy-2(1H)pyridone-6-carboxylic acid was suspended in 30 cc of water. To this suspension was added first 3 g of sodium carbonate and then 5 cc of isobutyl bromide. The reaction was carried out by stirring the mixture at 80° C for 40 hours. The reaction mixture was adjusted to pH 1.5 with 5N hydrochloric acid and extracted with 30 cc of chloroform. The extract was directly concentrated and the residue dissolved in 10 cc of ethyl ether and allowed to stand in the cold to precipitate crystals. The crystals were filtered off to obtain 540 mg of crystalline 3-isobutyloxy-2(1H)pyridone-6-carboxylic acid.

Melting point: 198°–199° C

Elemental analysis: Found (%): C 55.46, H 5.89, N 6.68; Calcd. for $C_{10}H_{13}O_4N$(%): C 56.86, H 6.20, N 6.63

EXAMPLE 11

To 1.5 g of 3-hydroxy-2(1H)pyridone-6-carboxylic acid and 2.5 g of potassium carbonate were added first 50 cc of water and then 1.5 g of trans-crotyl chloride. The mixture was stirred at room temperature for 3 hours. The reaction mixture (pH 8.5) was extracted with 20 cc of chloroform to remove impurities. The aqueous phase was adjusted to pH 1.5 with 5N hydrochloric acid and then extracted with 30 cc of chloroform. The extract was concentrated to approximately 3 cc. The concentrate, after addition of 10 cc of ethanol, was allowed to stand in the cold for precipitate crystals. The crystals were filtered off to obtain 1.1 g of 3-(2-butenyloxy)-2(1H)pyridone-6-carboxylic acid in the form of white crystals.

Melting point: 194°–196° C

Elemental analysis: Found (%): C 57.35, H 5.13, N 6.80; Calcd. for $C_{10}H_{11}O_4N$(%): C 57.41, H 5.30, N 6.70

EXAMPLE 12

1.5 g of 3-hydroxy-2(1H)pyridone-6-carboxylic acid was suspended in a mixture of 20 cc of water and 20 cc of methanol. To this suspension was added 1.2 g of sodium hydroxide, whereupon the carboxylic acid dissolved. Subsequently 4 cc of benzyl bromide was added and the mixture stirred at 60° C for 12 hours. The reaction mixture was adjusted to pH 1.8 with 5N hydrochloric acid and concentrated to approximately 8 cc, whereupon crystals precipitated. The crystals were recrystallized from chloroform/ethanol to obtain 1.8 g of 3-benzyloxy-2(1H)pyridone-6-carboxylic acid in the form of white needle-like crystals.

Melting point: 225°–226° C

Elemental Analysis: Found (%): C 63.20, H 4.65, N 5.57; Calcd. for $C_{13}H_{11}O_4N$(%): C 63.67, H 4.52, N 5.71

EXAMPLE 13

15 cc of water is added to 1.4 g of 3-hydroxy-2(1H)pyridone-6-carboxylic acid. Subsequently 2.3 g of sodium carbonate was added, whereupon the carboxylic acid dissolved. After 4 cc of p-chlorobenzyl chloride was added, the reaction was carried out by stirring the resulting mixture at 65° C, causing precipitation of crystals to take place. After a nine hour reaction, the reaction mixture was cooled and filtered to obtain 1.9 g of sodium 3-(p-chlorobenzyloxy)-2(1H)pyridone-6-carboxylate in the form of white crystals.

0.3 g of the product was dissolved in 30 cc of water and the solution adjusted to pH 1.8 with 5N hydrochloric acid and extracted with chloroform. The chloroform phase was directly concentrated to dryness. The residue was recrystallized from hot ethanol to obtain 0.2 g of 3-(p-chlorobenzyloxy)-2(1H)-pyridone-6-carboxylic acid in the form of white needle crystals.

Melting point: 219°–221° C

Elemental Analysis: Found %: C 56.12, H 3.63, N 4.98; Calcd. for $C_{13}H_{10}O_4N.Cl$(%): C 55.83, H 3.60, N 5.01

EXAMPLE 14

50 cc of water was added to 1.5 g of 3-hydroxy-2(1H)pyridone-6-carboxylic acid. Subsequently 3 g of sodium carbonate was added, whereupon the carboxylic acid dissolved. To the mixture was added dropwise, with stirring at 55° C over a period of 2 hours, 20 cc of ethanol containing 4 cc of p-ethylbenzyl chloride. After the reaction was continued at the same temperature for an additional 2 hours, the reaction mixture was concentrated to remove the ethanol.

The reaction mixture (pH 8) was extracted with 10 cc of chloroform to remove impurities, adjusted to pH 1.8 with 5N hydrochloric acid and extracted with 30 cc of chloroform. The chloroform extract was concentrated to approximately 30 cc. After addition of 8 cc of ethanol, the concentrate was allowed to stand in the cold, whereupon crystals precipitated. The crystals were filtered off to obtain 830 mg of 3-(p-ethylbenzyloxy)-2(1H)-pyridone-6-carboxylic acid in the form of white particulate crystals.

Melting point: 203°–204° C

Elemental analysis: Found (%): C 65.80, H 5.50, N 4.99; Calcd. for $C_{15}H_{15}O_4N$(%): C 65.92, H 5.53, N 5.13

EXAMPLE 15

3 g. of 3-hydroxy-2(1H)pyridone-6-carboxylic acid and 5 g of sodium carbonate were dissolved in 80 cc of water. To this mixture was added dropwise, with stirring at 50° C over a period of one hour, 20 cc of ethanol containing 7 cc of p-methylbenzyl chloride. After the reaction was continued at the same temperature for a further three hours, the reaction mixture was adjusted to pH 1.8 with 5N hydrochloric acid and extracted with 50 cc of chloroform.

The chloroform extract was concentrated to approximately 4 cc, and upon addition of 30 cc of ethyl ether precipitation of crystals took place. The crystals were recrystallized from chloroform/ethanol to obtain 1.2 g of 3-(p-methylbenzyloxy)-2(1H)-pyridone-6-carboxylic acid in the form of white needle crystals.

Melting point: 201°–202° C

Elemental analysis: Found (%): C 65.13, H 5.22, N 5.38; Calcd. for $C_{14}H_{13}O_4N$ (%): C 64.86, H 5.05, N 5.4

Further illustration of the invention is as follows:

One g of 3-hydroxy-2(1H) pyridone-6-carboxylic acid was suspended in a mixture of 15 cc pyridine and 5 cc propionic anhydride, followed by stirring at room temperature.

3-hydroxy-2(1H)pyridone-6-carboxylic acid dissolved slowly, precipitating reaction products.

After 24 hours, the reaction mixture was filtered off, to obtain 700 mg of 3-propionyl-2(1H)pyridone-6-carboxylic acid in the form of white powders.

What is claimed is:

1. A method for making a 3-substituted-2(1H)pyridone-6-carboxylic acid of the general formula

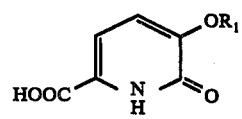

wherein R₁ represents a lower aliphatic acyl group, which comprises (a) reacting D-glucaro-δ-lactam or a metal salt of D-glucaro-δ-lactam with an anhydride in a reaction solvent that includes a base which induces acylation and dehydration reactions to occur simultaneously, and (b) heating the mixture formed by mixing said lactam or said metal salt with said anhydride in said solvent for from about 5 to 80 hours at temperatures from about 55° C to about 80° C, said base being selected from pyridine, piperidine and triethylamine, and said solvent being selected from pyridine, piperidine, triethylamine, dioxan and and dimethylformamide.

2. A method for making a 3-substituted-2(1H)pyridone-6-carboxylic acid of the general formula

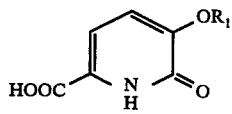

wherein R₁ is a straight chain alkyl group, a branched chain alkyl group, a straight chain alkenyl group, a branched chain alkenyl group, or an aralkyl group of the formula

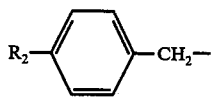

wherein R₂ is hydrogen, a lower alkyl group or a halogen, which comprises reacting 3-hydroxy-2(1H)pyridone-6-carboxylic acid with a halide of the general formula R₁X wherein R₁ is said above defined R₁ group and X is the halogen atom, the reaction with said halide being in the presence of a solvent and a base, said solvent being water, organic solvents miscible with water, or mixtures thereof, wherein said organic solvent is an alcohol, dioxan or acetone, and wherein said base is sodium hydroxide, potassium hydroxide, sodium carbonate, potassium carbonate, sodium hydrogen carbonate or an organic base, at reaction temperatures of from about 40° to about 100° C.

3. A method according to claim 1, which comprises, (a) mixing said D-glucaro-δ-lactam with said anhydride in said reaction solvent, and (b) heating the mixture of said lactam and said anhydride in said solvent for about five to seven hours at a temperature of about 55° C.

4. A method according to claim 1, which comprises (a) mixing said metal salt of D-glucaro-δ-lactam with said anhydride in said reaction solvemt, and (b) heating the mixture of said lactam salt and said anhydride in said solvent for about seventy to eighty hours at a temperature of about 80° C.

5. A method according to claim 1, wherein said base is pyridine, triethylamine or piperidine.

6. A method according to claim 1, wherein said solvent is dimethylformamide, dioxan, pyridine, triethylamine or piperdine.

7. A method according to claim 1, wherein said salt is the potassium salt of D-glucaro-δ-lactam and is mixed with acetic anhydride in pyridine which serves as both solvent and base and said heating is for about 70 hours at a temperature of 80° C.

8. A method according to claim 1, wherein said D-glucaro-δ-lactam is mixed with acetic anhydride in pyridine as both solvent and base and said heating is for about seven hours at a temperature of 60° C.

9. A method according to claim 1, wherein said salt is the potassium salt of D-glucaro-δ-lactam and is mixed with propionic anhydride in pyridine as both solvent and base and said heating is for about eighty hours at a temperature of 75° C.

10. A method according to claim 1, wherein said salt is the sodium salt of D-glucaro-δ-lactam and is mixed with butyric anhydride in pyridine as both solvent and base and said heating is for about fifty hours at a temperature of 90° C.

11. A method for making a 3-substituted-2(1H)pyridone-6-carboxylic acid of the general formula

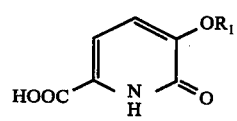

wherein R₁ is a straight chain alkyl group, a branched chain alkyl group, a straight chain alkenyl group, a branched chain alkenyl group, or an aralkyl group of the formula

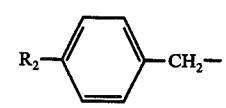

wherein R₂ is hydrogen, a lower alkyl group or a halogen, which comprises reacting 3-hydroxy-2(1H)pyridone-6-carboxylic acid with a halide of the general formula R₁X wherein R₁ is said above defined R₁ group and X is the halogen atom.

12. A method according to claim 11, in which said 3-hydroxy-2(1H)pyridone-6-carboxylic acid is reacted with said halide in the presence of a solvent and a base.

13. A method according to claim 12, wherein said solvent is water, organic solvents miscible with water, or mixtures thereof.

14. A method according to claim 13, wherein said organic solvent is an alcohol, dioxan or acetone.

15. A method according to claim 12, wherein said base is sodium hydroxide, potassium hydroxide, sodium carbonate, potassium carbonate, sodium hydrogen carbonate or an organic base.

16. A method according to claim 2, wherein said organic base is triethylamine.

17. A method according to claim 2, wherein said R₁ is the n-propyl group, said solvent is a mixture of ethanol and water, said base is sodium hydroxide and the temperature at which the reaction proceeds is 65° C.

18. A method according to claim 2, wherein said R₁ is the n-butyl group, said solvent is a mixture or methanol and water, said base is potassium hydroxide, and the temperature at which the reaction proceeds is 60° C.

19. A method according to claim 2, wherein said R₁ is the isobutyl group, said solvent is water, said base is sodium carbonate and said temperature at which the reaction proceeds is 80° C.

20. A method according to claim 2, wherein said R₁ is an alkenyl group and the reaction mixture formed by mixing 3-hydroxy-2(1H)pyridone-6-carboxylic acid with said halide in the presence of said solvent and base is at temperatures from room temperature to 70° C.

21. A method according to claim 20, wherein said $R_1$ is the allyl group, said solvent is water, said base is sodium carbonate and said temperature at which the reaction proceeds is 60° C.

22. A method according to claim 16, wherein said $R_1$ is the 2-butenyl group, said solvent is water, said base is potassium carbonate, and said temperature at which the reaction proceeds is room temperature.

23. Method according to claim 2, wherein said $R_1$ is said aralkyl group and the reaction mixture formed by mixing 3-hydroxy-2(1H)pyridone-6-carboxylic acid with said halide in the presence of said solvent and base is at temperatures from room temperature to 70° C.

24. A method according to claim 23, wherein said $R_1$ is the p-chlorobenzyl group, said solvent is water, said base is sodium carbonate, and said temperature at which the reaction proceeds is 65° C.

25. A method according to claim 23, wherein said $R_1$ is the p-ethylbenzyl group, said solvent is a mixture of water and ethanol, said base is sodium carbonate, and said temperature at which the reaction proceeds is 55° C.

26. A method according to claim 23, wherein said $R_1$ is the p-methylbenzyl group, said solvent is a mixture of ethanol and water, said base is sodium carbonate and said temperature at which the reaction proceeds is 50° C.

27. A method according to claim 11, in which said 3-hydroxy-2(1H)pyridone-6-carboxylic acid is reacted with said halide in the presence of an organic solvent and the product of their reaction is subsequently hydrolysed in the presence of acid or base as catalyst to form said desired 3-substituted-2(1H)pyridone-6-carboxylic acid.

* * * * *